United States Patent
Miki et al.

(10) Patent No.: US 10,188,540 B2
(45) Date of Patent: Jan. 29, 2019

(54) SACROILIAC BELT

(71) Applicant: BRACE FIT LLC, Owariasahi-shi, Aichi (JP)

(72) Inventors: Yasushi Miki, Nagoya (JP); Naoji Sakai, Toki (JP); Tomokazu Nasu, Owariasahi (JP); Keiichi Sakai, Toyoake (JP)

(73) Assignee: BRACE FIT LLC, Owariasahi (JP)

( * ) Notice: Subject to any disclaimer, the term of this patent is extended or adjusted under 35 U.S.C. 154(b) by 601 days.

(21) Appl. No.: 14/782,164

(22) PCT Filed: Apr. 4, 2014

(86) PCT No.: PCT/JP2014/059972
§ 371 (c)(1),
(2) Date: Oct. 2, 2015

(87) PCT Pub. No.: WO2014/163186
PCT Pub. Date: Oct. 9, 2014

(65) Prior Publication Data
US 2016/0058598 A1 Mar. 3, 2016

(30) Foreign Application Priority Data

Apr. 4, 2013 (JP) .................... 2013-078564

(51) Int. Cl.
| *A61F 5/02* | (2006.01) |
| *A62B 35/00* | (2006.01) |
| *A41F 9/00* | (2006.01) |

(52) U.S. Cl.
CPC ............. *A61F 5/028* (2013.01); *A41F 9/00* (2013.01); *A61H 2201/1652* (2013.01); *A62B 35/0006* (2013.01)

(58) Field of Classification Search
CPC . A61F 5/028; A61F 5/40; A62B 35/00; A62B 35/0006; A61H 2201/1652;
(Continued)

(56) References Cited

U.S. PATENT DOCUMENTS

| 4,985,937 A | 1/1991 | Blackburn |
| 5,179,942 A * | 1/1993 | Drulias .................. A61F 5/028 |
| | | 128/101.1 |

(Continued)

FOREIGN PATENT DOCUMENTS

| DE | 202012100457 U1 | 3/2012 |
| JP | H09-253107 A | 9/1997 |

(Continued)

OTHER PUBLICATIONS

Jul. 8, 2014 Search Report issued in International Patent Application No. PCT/JP2014/059972.

(Continued)

*Primary Examiner* — Keri J Nelson
(74) *Attorney, Agent, or Firm* — Oliff PLC

(57) ABSTRACT

Provided is a sacroiliac belt having a high holding ability for a user's pelvis as well as a high tightening effect to the user's sacroiliac joints. The sacroiliac belt has a belt pair that forms a pelvic holding loop to hold a user's pelvis. The belt pair has a ilium belt that is wound around the user's waist, and a second belt selected from either a buttock belt that is wound around the user's waist passing under the user's buttocks, lifting up the buttocks, or a lumbar belt that is wound around the user's waist, passing a back side of the user's lumbar curve located immediately above the pelvis. Both ends of the second belt are each connected to the ilium belt inside both ends of the ilium belt.

8 Claims, 6 Drawing Sheets

(58) Field of Classification Search
CPC .. A41F 9/00; A41F 9/002; A41F 11/00; A41F 11/16
USPC ......... 602/19, 70; 128/875, 876; 2/311, 312, 2/318, 319, 321
See application file for complete search history.

(56) References Cited

U.S. PATENT DOCUMENTS

| | | | |
|---|---|---|---|
| 5,406,942 | A | 4/1995 | Loo |
| 5,782,781 | A | 7/1998 | Nagaoka |
| 5,896,859 | A * | 4/1999 | Carroll ................. A61G 7/1023 128/845 |
| 6,427,374 | B1 * | 8/2002 | Vaiani .................... F41C 23/02 119/770 |
| 2007/0232973 | A1 | 10/2007 | Serola |
| 2007/0232974 | A1 | 10/2007 | Serola |
| 2013/0333706 | A1 | 12/2013 | Bauerfeind |

FOREIGN PATENT DOCUMENTS

| | | |
|---|---|---|
| JP | H11-104159 A | 4/1999 |
| JP | H11-290362 A | 10/1999 |
| JP | 2009-100865 A | 5/2009 |
| JP | 2009-160027 A | 7/2009 |
| JP | 2009-532186 A | 9/2009 |

OTHER PUBLICATIONS

May 4, 2016 Office Action issued in Chinese Patent Application No. 201480018701.6.
Jan. 28, 2016 Extended Search Report issued in European Patent Application No. 14778992.9.

* cited by examiner

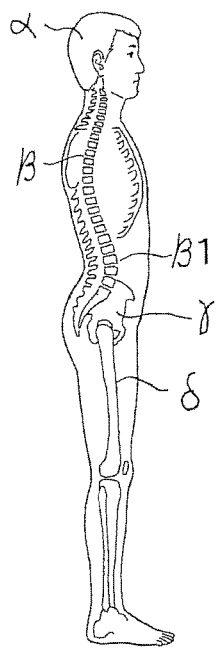
FIG. 7A
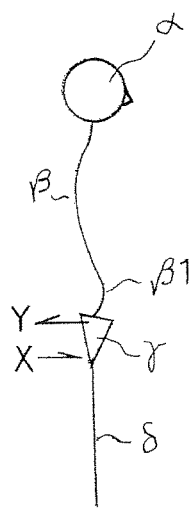 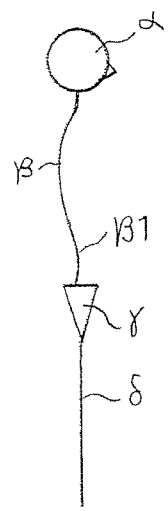 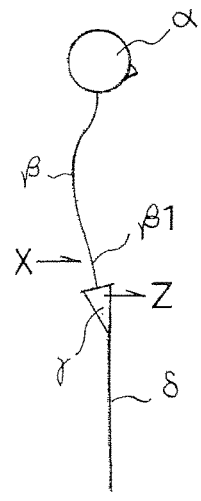
FIG. 7B　　FIG. 7C　　FIG. 7D

US 10,188,540 B2

SACROILIAC BELT

TECHNICAL FIELD

The present invention relates to a sacroiliac belt that comprises an ilium belt wound around a sacroiliac joints of a user's pelvis and either a buttock belt passing under the user's buttocks, lifting up the buttocks, or a lumbar belt wound around the waist passing the user's lumbar back. The sacroiliac belt corrects pelvic anteversion and excellently holds the pelvis.

BACKGROUND ART

A pelvis contains a sacrum and a pair of ilia connected to right and left sides of the sacrum. The ilia are connected to the sacrum by a pair of sacroiliac joints located at a bottom end of a lumbar. The sacroiliac joints serve as firm joints, surrounded by ligaments, while the joints allow slight motions of several millimeters. The slight motions of the sacroiliac joints help a human body to keep a balance depending on various body motions in daily life. Thus, the sacroiliac joints support the lumbar at the bottom thereof.

When a load is placed on the sacroiliac joints during an unnatural body motion such as a work in a stooping position, the load may cause a slight displacement in the sacroiliac joints such as loosening and twisting thereof. The slight displacement may induce a change in a position or an angle of the pelvis, which directly supports the bottom of the lumbar. Typical examples of the change in the position or the angle of the pelvis include pelvic abnormalities such as "anteversion" and "retroversion".

The changes in the position or the angle of the pelvis may hinder proper support for the lumbar by the sacroiliac joints, and thus may cause a damage to the sacroiliac joints such as a lower back pain. The damage in the sacroiliac joints may become a cause of a chronic lower back pain if the damage persists without reduced. Further, a damage in the sacroiliac joints caused by loosening thereof is often regarded as relating to a lower back pain of a woman after giving birth.

To solve the problems, various types of sacroiliac belts for protecting the sacroiliac joints, which are also referred to as waist corsets, waist supporters, sacroiliac correction belts, or pelvic protection belts, have conventionally been proposed.

For example, PTL1 discloses a waist corset comprising a fixing portion and a belt portion. The fixing portion has a large width, and is worn on a user's belly. The belt portion extends from the fixing portion, and is wound around the user's waist. Ends of the belt portion can be bonded to the fixing portion via touch fasteners.

PTL2 discloses a belt for correction of movement in sacroiliac joint capsules. The belt has an adjustable length to be wound around a user's waist, having a part made of an elastic material. The belt has a pressing member on an inner surface thereof at a position which is in contact with an area between the user's posterior superior and inferior iliac spines when the belt is wound around the waist at a specific height corresponding to the ilia.

Further, PTL3 discloses a lumbar belt comprising a main belt, a pair of fastening belts, and a hanging belts. The pair of fastening belts helps fastening of the main belt when the main belt is wound around the waist. The hanging belts extend upward from the main belt like suspenders, and maintain the position of the main belt around the waist even when the main belt is not fastened.

CITATION LIST

Patent Literature

PTL1: JP 2009-160027 A
PTL2: JP 2009-100865 A
PTL3: JP Hei11-104159 A

SUMMARY OF INVENTION

Technical Problem

The conventional sacroiliac belts described above each form single rings around the user's waist when wound around the waist. Though the lumbar belt disclosed in PTL 3 has the fastening belt in addition to the main belt, the lumbar belt also substantially forms a single ring around the user's waist when wound around the waist because the fastening belts overlap the main belt to enhance tightening pressure of the main belt. These conventional sacroiliac belts are wound around the user's waist in a state where the belts surround the user's right and left ilia in order to tighten the sacroiliac joints.

The present inventors, however, found that a sacroiliac belt wound around the waist in the form of a single ring has a low holding ability for the pelvis. The term "holding ability" for the pelvis means an ability of the sacroiliac belt to hold the entire pelvis like wrapping the pelvis, as well as to apply tightening pressure to the sacroiliac joints. A belt having a low holding ability can not sufficiently prevent anteversion or retroversion of the pelvis caused by a load to the sacroiliac joints. Further, the belt having the low holding ability is easy to be displaced from a correct position with respect to the pelvis when the user sits or crouches down. Furthermore, the sacroiliac belt wound around the waist in the form of the single ring does not have a sufficient effect to correct the anteversion or retroversion that already exists.

The present invention has been made in view of the problems described above, and an object of the present invention is to provide a sacroiliac belt that sufficiently prevents and corrects anteversion and retroversion of a pelvis, having a high holding ability for the pelvis as well as a high tightening effect to sacroiliac joints, and is hard to be displaced from a correct position even when a user sits or crouches down.

Solution to Problem (First Invention)

To achieve the objects and in accordance with the purpose of the present invention, a sacroiliac belt according to a first invention has a belt pair that forms a pelvic holding loop to hold a user's pelvis. The belt pair has:

a ring-shaped ilium belt (A) that is wound around the user's waist, surrounding the user's right and left ilia; and a second belt selected from:

either a ring-shaped buttock belt (B1) that is separate from the ilium belt (A), and is wound around the user's waist passing under the user's buttocks, lifting up the buttocks; or a ring-shaped lumbar belt (B2) that is separate from the ilium belt (A), and is wound around the user's waist passing aback side of the user's lumbar curve located immediately above the pelvis.

(Second Invention)

To achieve the objects and in accordance with the purpose of the present invention, a sacroiliac belt according to a second invention has a belt pair that forms a pelvic holding loop to hold a user's pelvis. The belt pair has:

a ring-shaped ilium belt (A) that is wound around the user's waist, surrounding the user's right and left ilia; and a second belt selected from:

either a ring-shaped buttock belt (B1) that is wound around the user's waist passing under the user's buttocks, lifting up the buttocks; or a ring-shaped lumbar belt (B2) that is wound around the user's waist passing a back side of the user's lumbar curve located immediately above the pelvis. The ilium belt (A) and the second belt are integrally connected to each other.

(Third Invention)

To achieve the objects and in accordance with the purpose of the present invention, a sacroiliac belt according to a third invention has a belt pair that forms a pelvic holding loop to hold a user's pelvis. The belt pair has:

a ring-shaped ilium belt (A) that is wound around the user's waist, surrounding the user's right and left ilia; and a second belt selected from:

either a buttock belt (B1) that is wound around the user's waist passing under the user's buttocks, lifting up the buttocks; or a lumbar belt (B2) that is wound around the user's waist passing a back side of the user's lumbar curve located immediately above the pelvis.

The second belt is shorter than the ilium belt. Both ends of the second belt are each connected to the ilium belt in a pair of connection areas placed inside both ends of the ilium belt.

(Fourth Invention)

To achieve the objects and in accordance with the purpose of the present invention, a sacroiliac belt according to a fourth invention is based on the sacroiliac belt according to the third invention. The pair of connection areas is placed in boundary regions between front and back sides of the ilium belt for connecting the ilium belt and the buttock belt, and the pair of connection areas is placed in a central region of the frond side of the ilium belt for connecting the ilium belt and the lumbar belt.

(Fifth Invention)

To achieve the objects and in accordance with the purpose of the present invention, a sacroiliac belt according to a fifth invention is based on the sacroiliac belt according to the third or fourth invention. The sacroiliac belt has a connection between the ilium belt and the second belt that is selected from:

(1) A fixed connection through which the both ends of the second belt are connected and fixed to the pair of connection areas on the ilium belt;

(2) A reversible connection through which the both ends of the second belt are reversibly connected to the pair of connection areas on the ilium belt via touch fasteners that consist of first and second components, the first components attached in the connection areas on the ilium belt, the second components attached on the both ends of the second belt; and (3) The reversible connection (2), wherein the first components have widths within which positions of connection between the first and second components are adjustable.

In the present inventions, "touch fasteners" means a pair of fastener components that are attached on two sheet-shaped members to be reversibly face-bonded to each other. For example, one of the fastener components has a large number of minute loops while the other has a large number of minute hooks. Touch fasteners called "Magic Tapes" (registered trademark) are popular; however, the touch fasteners used in the present inventions are not specifically limited thereto. In the present specification, "bonding" a member to another member "via touch fasteners" means reversibly face-bonding the two members with the use of the touch fasteners described above.

(Sixth Invention)

To achieve the objects and in accordance with the purpose of the present invention, a sacroiliac belt according to a sixth invention is based on the sacroiliac belt according to the fifth invention. The connection between the ilium belt and the second belt is either the connection (2) or the connection (3). The sacroiliac belt has rings at the both ends of the second belt, and the ilium belt and the second belt are reversibly connected to each other via the touch fasteners while the ilium belt placed through the rings.

(Seventh Invention)

To achieve the objects and in accordance with the purpose of the present invention, a sacroiliac belt according to a seventh invention is based on the sacroiliac belt according to anyone of the first to sixth inventions. In the sacroiliac belt;

(4) At least a part of the ilium belt or the second belt is made of an elastic material, or (5) At least a part of the ilium belt or the second belt is made of an elastic material, and the part has a double-belt structure.

(Eighth Invention)

To achieve the objects and in accordance with the purpose of the present invention, a sacroiliac belt according to an eighth invention is based on the sacroiliac belt according to any one of the first to seventh inventions. The sacroiliac belt has an auxiliary belt that is attached to the ilium belt and increases a tightening pressure of the ilium belt.

Advantageous Effects of Invention (First to Third Inventions)

The sacroiliac belt according to any one of the first to third inventions has the second belt selected from either the buttock belt that is wound around the user's waist passing under the user's buttocks, lifting up the buttocks, or the lumbar belt that is wound around the user's waist passing the back side of the lumbar curve located immediately above the pelvis, as well as the ring-shaped ilium belt that is wound around the user's waist, surrounding the user's right and left ilia. Effects of the sacroiliac belt are explained based on FIGS. 7A to 7D.

FIG. 7A shows a skeletal frame of a human body facing right in an upright position. FIGS. 7B to 7D show the skeletal frame in the form of simple illustrations, each including only a head α, a lumbar β, a pelvis γ, and legs δ. FIG. 7B shows an abnormal state called "anteversion". In the state, the lumbar curve β1, which is located immediately above the pelvis γ, has an excessively high curvature toward the front, and thus the pelvis γ is inclined toward the front. FIG. 7C shows a normal state. FIG. 7D shows an abnormal state called "retroversion". In the state, the lumbar curve β1, which is located immediately above the pelvis γ, has an excessively low curvature toward the front, and thus the pelvis γ is inclined toward the back.

The sacroiliac belt having the ilium belt and the buttock belt is effective on a user who has an anteversion of the pelvis as shown in FIG. 7B. While the ilium belt tightens the sacroiliac joints, the buttock belt pushes a lower portion of the pelvis γ toward the direction X. Thus, an upper portion of the pelvis γ is displaced toward the direction Y relatively. As a result, the sacroiliac belt has an effect to correct the pelvic anteversion into the normal state shown in FIG. 7C.

Further, the ilium belt and the buttock belt form a buttock-side pelvic holding loop to hold the entire pelvis from a buttock side, like wrapping the pelvis, while preventing the pelvic anteversion. Thus, the sacroiliac belt has a high holding ability for the pelvis.

The sacroiliac belt having the ilium belt and the lumbar belt is effective on a user who has a retroversion of the pelvis as shown in FIG. 7D. While the ilium belt tightens the sacroiliac joints, the lumbar belt pushes a lumbar back, which is a back side of the lumbar curve β1 immediately above the pelvis γ, toward the direction X. Thus, the upper portion of the pelvis γ is displaced toward the direction Z. As a result, the sacroiliac belt has an effect to correct the pelvic retroversion into the normal state shown in FIG. 7C. Further, the ilium belt and the lumbar belt form a lumbar-side pelvic holding loop to hold the entire pelvis from the lumbar back side, like wrapping the pelvis, while preventing the pelvic retroversion. Thus, the sacroiliac belt has a high holding ability for the pelvis.

Thus, the sacroiliac belt have novel effects in addition to protection effect to the sacroiliac joints as conventional sacroiliac belts have because the belt has a high holding ability for the pelvis. Specifically, a novel effect is that the sacroiliac belts sufficiently prevents and corrects pelvic anteversion and retroversion due to various loads to the sacroiliac joints. Another novel effect is that the belt, wound around the waist, is hard to be displaced from a correct position with respect to the pelvis when the user sits or crouches down.

In the sacroiliac belt according to the first invention, the ring-shaped ilium belt and the ring-shaped buttock or lumbar belt are separate from each other. Meanwhile, in the sacroiliac belts according to the second and third inventions, the ilium belts and the buttock or lumbar belts are connected to each other. Thus, the sacroiliac belts according to the second and third inventions are more convenient in storage and distribution, and are more easily put on by the user than the sacroiliac belt according to the first invention.

Especially, in the sacroiliac belt according to the third invention, the buttock or lumbar belt is shorter than the ilium belt, and the both ends of the buttock or lumbar belt are each connected to the ilium belt in the pair of connection areas placed inside the both ends of the ilium belt. Thus, the ilium belt and the buttock or lumbar belt form a relatively small buttock- or lumbar-side pelvic holding loop (i.e., a pelvic holding loop having a size to hold the pelvis from a buttock side or a lumbar back side appropriately).

Thus, the sacroiliac belt has an especially high holding effect to the pelvis in the state of anteversion or retroversion. Further, the sacroiliac belt is especially hard to be displaced with respect to the pelvis from the correct position when the user sits or crouches down.

For purpose of reference, it should be noted that the buttock or lumbar belts of the sacroiliac belts according to the first to third inventions may also be wound around the user's waist, surrounding the right and left ilia, in the same way as the ilium belts.

(Fourth Invention)

When the pair of connection areas is placed in the boundary regions between the front and back sides of the ilium belt for connecting the ilium belt and the buttock belt, the sacroiliac belt can hold the pelvis from the buttock side in a more compact manner. When the connection areas are placed in a central region of the front side of the ilium belt for connecting the ilium belt and the lumbar belt, the lumbar belt can be wound around the waist at a position as high as the lumbar back without great difficulty. Further, since the front side of the lumbar belt does not reach the upper portion of the user's femurs, the lumbar belt does not affect the user's walking motion.

(Fifth Invention)

The connection between the ilium belt and the buttock or lumbar belt is not specifically limited; however, the connections (1) to (3) in the fifth inventions are preferable. Among them, the connection (2) is convenient for putting on and taking off of the sacroiliac belt since the connection is reversible. Especially, in the connection (3), a position of the connection between the ilium belt and the buttock or lumbar belt can be changed. Thus, the position can be easily adjusted to form a pelvic holding loop having an appropriate size according to the user's physique and body shape.

(Sixth Invention)

In the sixth invention, which has either the connection (2) or the connection (3) of the fifth invention, the sacroiliac belt has the rings at the both ends of the buttock or lumbar belt, and the ilium belt and the buttock or lumbar belt are reversibly connected to each other via the touch fasteners while the ilium belt is placed through the rings. The rings allow a play in a connection angle between the two belts. Thus, the connection angle of the buttock or lumbar belt to the ilium belt can be changed freely while the two belts are connected to each other firmly through the touch fasteners. Accordingly, the buttock belt can be easily wound around the waist passing under the user's buttocks without great difficulty while the lumbar belt can be easily wound around the waist passing the lumbar back without great difficulty.

For example, when the sacroiliac belt has sheet-shaped touch fasteners in the connection areas of the ilium belt and on the both ends of the buttock or lumbar belt along planes of the belts, a strong connection can be achieved by parallel overlapping and bonding of the touch fasteners. In this case, it is difficult to provide a connection angle between the two belts with which the buttock belt passes under the buttocks or the lumbar belt passes the lumbar back. However, the sixth invention solves the problem since the rings allow the play in the connection between the two belts.

Further, using the rings, the second components of the touch fasteners attached on the buttock or lumbar belt can be bonded to the first component attached on the ilium belt on an outer surface of the ilium belt while the buttock or lumbar belt is placed inside an inner surface of the ilium belt. Thus, the buttock or lumbar belt is hardly disconnected from the ilium belt without the user's intention while very easily disconnected from the ilium belt by the user's intention.

In a modification of the above-described connection between the ilium belt and the buttock or lumbar belt via rings, the sacroiliac belt may have a pair of rings in the connection areas on the ilium belt for connecting the buttock or lumbar belt, instead of having the rings at the both ends of the buttock or lumbar belt. The two belts are reversibly connected to each other via the touch fasteners while the both ends of the buttock or lumbar belt are placed through the rings. In this case, however, "an effect to allow the connection angle of the buttock or lumbar belt to the ilium belt to be changed freely" is less sufficient.

(Seventh Invention)

At least a part of the ilium belt or the buttock or lumbar belt may be made of the elastic material as in the configuration (4) of the seventh invention. In this case, the sacroiliac belt can provide a comfortable tightening pressure by a high elasticity of the belt. Further, the part of the ilium belt or the buttock or lumbar belt made of the elastic material may has the double-belt structure as in the configuration (5) of the seventh invention. In this case, the sacroiliac belt can provide a higher tightening pressure by high elasticity of the belt.

(Eighth Invention)

The sacroiliac belt may have the auxiliary belt that is attached to the ilium belt and increases the tightening pressure of the ilium belt. The sacroiliac belt can provide an especially high tightening pressure with the auxiliary belt.

At least a part of the auxiliary belt may also be made of an elastic material.

The auxiliary belt may be connected to the ilium belt via rings attached on both ends of the auxiliary belt, like the buttock or lumbar belt in the sixth invention. Alternatively, in a modification, the sacroiliac belt may have a pair of rings in auxiliary connection areas on the ilium belt for connecting the auxiliary belt, instead of having the rings at the both ends of the auxiliary belt. The ilium belt and the auxiliary belt are reversibly connected to each other via touch fasteners while the both ends of the auxiliary belt are placed through the rings.

BRIEF DESCRIPTION OF DRAWINGS

FIG. 7A shows a skeletal frame of a human body facing right in an upright position. FIGS. 7B to 7D show the skeletal frame in the form of simple illustrations, each including only a head, a lumbar, a pelvis, and legs.

Figure 1A:
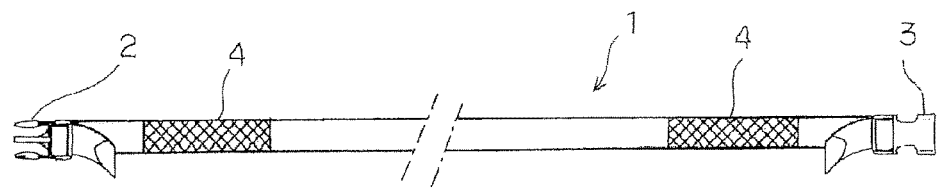
FIG. 1A is a front view showing an ilium belt (i.e., a view of an outer surface of the ilium belt).

DESCRIPTION OF REFERENCE NUMERALS 1 ilium belt
1a ilium belt
a stopper bar
b buckle ring
2 hook
3 bracket
4 sheet-shaped fastener component
5 buttock/lumbar belt
5a buttock/lumbar belt
5b buttock belt
5c lumbar belt
6 sheet-shaped fastener component
7 ring
8 auxiliary belt
8a auxiliary belt
9 sacroiliac belt
10 connector
11 connection structure via ring
12 touch fastener structure
13a buttock-side pelvic holding loop
13b lumbar-side pelvic holding loop
14 sacroiliac belt
15 fixed connection
16 sacroiliac belt
17 double-belt structure
α head
β lumbar
β1 lumbar curve
γ pelvis
δ legs

DESCRIPTION OF EMBODIMENTS

A detailed description of preferred embodiments of the present invention will now be provided including best embodiments.

[Sacroiliac Belt]

A sacroiliac belt according to a preferred embodiment of the present invention contains an ilium belt and either a buttock belt or a lumbar belt. The ilium belt is wound around a user's waist, surrounding the user's right and left ilia. The buttock belt is wound around the user's waist passing under the user's buttocks, lifting up the buttocks. The lumbar belt is wound around the user's waist passing the user's lumbar back, which is a back side of the user's lumbar curve located immediately above the pelvis. The ilium belt is preferably wound around the waist passing immediately below portions where the right and left ilia protrude toward the front (i.e., toward the ventral side of the user).

When the sacroiliac belt is worn on the user's body, the ilium belt and the buttock or lumbar belt form a pelvic holding loop that holds the user's pelvis. The "pelvic holding loop" means a buttock- or lumbar-side pelvic holding loop described below.

The buttock-side pelvic holding loop is a loop structure formed when the sacroiliac belt that has the ilium belt and the buttock belt is worn on the user's body. The ilium belt is wound around the user's waist, surrounding the user's right and left ilia, while the buttock belt is wound around the user's waist passing under the user's buttocks, lifting up the buttocks. The buttock-side pelvic holding loop holds the pelvis from the buttock side, like wrapping the entire pelvis.

The lumbar-side pelvic holding loop is a loop structure formed when the sacroiliac belt that has the ilium belt and the lumbar belt is worn on the user's body. The ilium belt is wound around the user's waist, surrounding the user's right and left ilia, while the lumbar belt is wound around the user's waist passing the lumbar back, which is the back side of the lumbar curve located immediately above the pelvis. The lumbar-side pelvic holding loop holds the pelvis from the lumbar back side, like wrapping the entire pelvis.

Sacroiliac Belts According to First to Third Preferred Embodiments

A sacroiliac belt according to a first preferred embodiment of the present invention has two separate ring-shaped belts having lengths sufficient to be wound around the user's waist. One of the ring-shaped belts is used as the "ilium belt wound around the user's waist, surrounding the user's right and left ilia". The other of the ring-shaped belts is used either as the "buttock belt wound around the user's waist passing under the user's buttocks, lifting up the buttocks", or as the "lumbar belt wound around the user's waist passing the user's lumbar back, which is the back side of the lumbar curve located immediately above the pelvis".

When used in the above-described ways, the two belts form the buttock- or lumbar-side pelvic holding loop. It is preferable that each of the two belts has a pair of reversible connectors having an appropriate connection mechanism (such as consisting of a hook and a bracket) at both ends of the belt. Each of the belts forms a ring via the pair of connectors when worn on the user's body. The type of the connectors is not specifically limited.

In a second preferred embodiment of the present invention, the two ring-shaped belts (having the lengths sufficient to be wound around the user's waist) contained in the first embodiment are integrally connected to each other at one or more sites (e.g., at central portions of the belts). The belts may be connected to each other through a fixed connection (such as by sewing), or through a reversible connection (such as by touch fasteners).

A third embodiment of the present invention is especially preferred. In the third embodiment, the buttock or lumbar belt is shorter than the ilium belt. Both ends of the buttock or lumbar belt are each connected to the ilium belt in the pair of connection areas placed inside the both ends of the ilium belt. The ilium belt in the third embodiment also has a length sufficient to be wound around the user's waist. It is preferable that the ilium belt has a pair of reversible connectors having an appropriate connection mechanism (such as consisting of a hook and a bracket) at both ends of the ilium belt. The ilium belt forms a ring with the connectors when worn on the user's body. The type of the connectors is not specifically limited. In the third embodiment, the ilium belt and the buttock or lumbar belt integrally form a buttock- or lumbar-side pelvic holding loop having a small size that holds the user's pelvis from the buttock side or from the lumbar back side excellently.

Connection Between Ilium Belt and Buttock or Lumbar Belt in Third Embodiment

In the above-described third embodiment, the ilium belt and the buttock or lumbar belt may be connected to each other in a way selected from the following options.

(1) The both ends of the buttock or lumbar belt are connected and fixed to the pair of connection areas on the ilium belt through a fixed connection. Here, preferable examples of the "fixed connection" include a connection by sewing of the both ends of the buttock or lumbar belt to the ilium belt in the connection areas, or a connection with the use of appropriate instruments to fix the belts to each other; however, the fixed connection is not limited specifically.

(2) The both ends of the buttock or lumbar belt are reversibly connected to the pair of connection areas on the ilium belt through a reversible connection via touch fasteners. The touch fasteners consist of first and second components. The first components are attached in the connection areas on the ilium belt while the second components are attached on the both ends of the second belt. However, any means to provide the reversible connection other than the touch fasteners may also be used.

(3) Based on the reversible connection (2), the first components have widths within which positions of connection between the first and second components are adjustable.

[Ilium Belt]
(Embodiment of Ilium Belt)

The ilium belt may be a flexible and strong band-shaped belt having no elasticity, made of a natural or synthetic fiber, though the material of the belt is not specifically limited. The ilium belt may have a width of 1 to 4 cm, though the width is not specifically limited, either. A pair of connectors having an appropriate connection mechanism such as consisting of a hook and a bracket is attached on both ends of the ilium belt. For convenience in putting on and taking off of the ilium belt, the hook and the bracket are preferably placed on the front side of the user's body when the ilium belt is wound around the user's body.

In the third embodiment described above, the pair of connection areas in which the both ends of the buttock or lumbar belt are connected to the ilium belt is placed inside the both ends of the ilium belt. The both ends of the buttock or lumbar belt may be connected to the ilium belt in the connection areas through the fixed connection such as by sewing. Alternatively, for reversible connection, first components of touch fasteners may be attached in the connection areas.

For the reason already described in the section of "Advantageous Effects of Invention" for the fourth invention, the pair of connection areas is placed in boundary regions between front and back sides of the ilium belt for connecting the ilium belt and the buttock belt to each other while the pair of connection areas is placed in a central region of the frond side of the ilium belt for connecting the ilium belt and the lumbar belt to each other.

When the first components of the touch fasteners attached in the connection areas on the ilium belt have wide widths, positions of the connection of the both ends of the buttock or lumbar belt to the ilium belt can be changed freely. Thus, the size of the buttock- or lumbar-side pelvic holding loop can be adjusted freely even with the use of an identical buttock or lumbar belt. Further, when a part of the buttock or lumbar belt is made of an elastic material, a tension strength (i.e., a degree of the holding ability for the pelvis) can be adjusted when the belt is worn on the user's body.

[Use of Elastic Material in Ilium Belt]

At least a part of the ilium belt, such as a central portion which is placed on the back side of the user's body when the ilium belt is worn on the user's body, is preferably made of a band-shaped elastic material, instead of the above-mentioned strong belt having no elasticity. Preferable examples of the band-shaped elastic material include the following materials (a) to (c).

(a) A material that is made by loosely weaving a natural or synthetic fiber to have elasticity, and by mixing a rubber yarn with the woven material. The mixed material as a whole has elasticity.

(b) A band-shaped rubber material.

(c) A material containing a belt-shaped core made of a rubber material and a tube-shaped material made by loosely weaving a natural or synthetic fiber to have elasticity. The belt-shaped core is held in the tube-shaped material.

Among them, a material exposing a rubber material such as the material (a) or (b) hardly causes displacement of the ilium belt from a correct position when worn on the user's body since the belt has high frictional resistance on an underwear placed under the belt and a shirt or trousers placed over the belt.

When the at least the part of the ilium belt is made of the elastic material, the part may preferably have a double-belt structure to provide a strong tightening pressure to the ilium belt by high elasticity of the material.

[Buttock or Lumbar Belt]

(Embodiment of Buttock or Lumbar Belt)

The buttock or lumbar belt may also be a flexible and strong band-shaped belt having no elasticity made of a natural or synthetic fiber, though the material of the belt is not specifically limited. The buttock or lumbar belt may have a width of 1 to 4 cm, though the width is not specifically limited, either. In the fourth embodiment described above, the buttock belt is relatively short while the lumbar belt is relatively long.

In the above-described third embodiment, the both ends of the buttock or lumbar belt are each connected to the pair of connection areas on the ilium belt, through the fixed connection such as by sewing, or through the reversible connection such as via touch fasteners.

(Use of Elastic Material in Buttock or Lumbar Belt)

At least a part of the buttock or lumbar belt, such as a central portion which is placed on the back side of the user's body when the belt is worn on the user's body, is preferably made of a band-shaped elastic material, instead of the above-mentioned strong belt having no elasticity. Preferable examples of the band-shaped elastic material include the materials (a) to (c) described above for the ilium belt. Among them, a material that exposes a rubber material such as the material (a) or (b) hardly causes displacement of the buttock or lumbar belt from a correct position when worn on the user's body since the belt has high frictional resistance on an underwear placed under the belt and a shirt or trousers placed over the belt.

When the at least the part of the buttock or lumbar belt is made of the elastic material, the part may preferably have a double-belt structure to provide a strong tightening pressure to the buttock or lumbar belt by high elasticity of the material.

(Use of Rings with Buttock or Lumbar Belt)

In the connections (2) and (3) of the third embodiment described above, the sacroiliac belt preferably has rings a little more inside the both ends of the buttock or lumbar belt than the second components of the touch fasteners attached on the both ends. The ilium belt is put through the rings. Then, the ilium belt and the buttock or lumbar belt are reversibly connected to each other via the touch fasteners.

When the first and second components of the touch fasteners are attached in the connection areas on the ilium belt and on the both ends of the buttock or lumbar belt, respectively, along the planes of the belts, strongest connections are achieved between the fastener components when the fastener components are bonded to each other in a parallel arrangement. In this case, however, it is usually difficult to provide connection angles with which the buttock belt passes under the user's buttocks or the lumbar belt passes the user's lumbar back. The above-described rings allow the buttock or lumbar belt to freely set the connection angles. Thus, the connection angles with which the buttock belt passes under the user's buttocks or the lumbar belt passes the lumbar back are easily provided.

From another point of view, when the ilium belt and the buttock or lumbar belt are connected to each other via the touch fasteners, worn on the user's body, the main portion of the buttock or lumbar belt (i.e., a portion passing under the buttocks or passing the lumbar back) is preferably placed inside the inner surface of the ilium belt while the buttock or lumbar belt preferably overlaps the ilium belt on the outer surface of the ilium belt in the connection areas. The configuration allows the buttock or lumbar belt to be easily put on and taken off from the ilium belt. The above-described rings enable the configuration.

[Attachment of Auxiliary Belt to Ilium Belt]

(Embodiment of Auxiliary Belt)

It is preferable that an auxiliary belt is attached to the ilium belt to enhance the tightening pressure of the ilium belt on the user's pelvis. Both ends of the auxiliary belt are connected to auxiliary connection areas placed on the ilium belt inside the both ends thereof through fixed or reversible connection, as in the case of the buttock or lumbar belt. On the other hand, the auxiliary belt is different from the buttock or lumbar belt in that the auxiliary belt is wound around the user's waist, surrounding the right and left ilia, overlapping the ilium belt.

The auxiliary belt may also be a flexible and strong band-shaped belt having no elasticity made of a natural or synthetic fiber, though the material of the belt is not specifically limited. The auxiliary belt may have a width of 1 to 4 cm, though the width is not specifically limited, either.

(Use of Elastic Material in Auxiliary Belt)

At least a part of the auxiliary belt, such as a central portion which is placed on the back side of the user's body when the belt is worn on the user's body, is preferably made of a band-shaped elastic material, instead of the above-mentioned strong belt having no elasticity. Preferable examples of the band-shaped elastic material include the materials (a) to (c) de scribed above for the ilium belt. Among them, a material that exposes a rubber material such as the material (a) or (b) hardly causes displacement of the auxiliary belt from a correct position when worn on the user's body since the belt has high frictional resistance on an underwear placed under the belt and a shirt or trousers placed over the belt.

When the at least the part of the auxiliary belt is made of an elastic material, the part may preferably have a double-belt structure to provide a strong tightening pressure to the auxiliary belt by high elasticity of the material.

(Use of Rings with Auxiliary Belt)

When components of touch fasteners are attached on the both ends of the auxiliary belt for connection to the auxiliary connection areas on the ilium belt, the sacroiliac belt preferably has rings placed a little more inside the both ends of the auxiliary belt than the fastener components. The ilium belt is put through the rings. Then, the ilium belt and the auxiliary belt are reversibly connected to each other via the touch fasteners.

The use of the rings for the connection of the auxiliary belt to the ilium belt has no technical effect to "allow the auxiliary belt to freely set the connection angles to the ilium belt", as in the case of the buttock or lumbar belt. The rings, however, allow the auxiliary belt to be placed inside the inner surface of the ilium belt while allowing the fastener components attached on the both ends of the auxiliary belt to overlap the ilium belt on the outer surface of the ilium belt in the auxiliary connection areas. Thus, the rings allow the auxiliary belt to be easily put on and taken off from the ilium belt.

Example

A description of the present invention will now be specifically provided with reference to Examples. It is to be noted that the present invention is not limited to Examples.

[Ilium Belt]

Figure 1B:
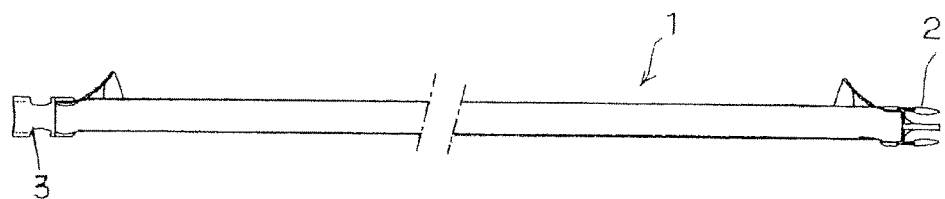
FIG. 1B is a rear view showing the ilium belt (i.e., a view of an inner surface of the ilium belt).

An ilium belt is a belt wound around a user's waist, surrounding right and left ilia of the user. FIG. 1A is a front view showing the ilium belt (i.e., a view of an outer surface of the ilium belt when worn on the use's body). FIG. 1B is a rear view showing the ilium belt (i.e., a view of an inner surface of the ilium belt when worn on the use's body). The ilium belt 1 is a flexible and strong band-shaped belt having no elasticity made of a natural or synthetic fiber. The ilium belt 1 has a length sufficient to be wound around the user's waist, and a width of about 2 cm. A hook 2 and a bracket 3, which constitute a pair of conventional connectors, are attached on both ends of the ilium belt 1.

The hook 2 and the bracket 3 each have buckles that have buckle rings b and stopper bars a placed in the centers of the buckle rings b. The both ends of the ilium belt 1 are fixed to the hook 2 and the bracket 3 by the buckles. When the ilium belt 1 is wound around the user's waist, the both ends of the ilium belt 1 are reversibly connected to each other via the hook 2 and the bracket 3 on the front side of the user's body.

A pair of connection areas is placed on the outer surface of the ilium belt a little inside the both ends of the belt 1. Sheet-shaped fastener components 4,4 having certain lengths are attached in the pair of connection areas for connecting both ends of the below-described buttock or lumbar belt thereto. Each of the fastener components 4,4 consists of one of paired components of touch fasteners (e.g., a sheet-shaped component having a large number of minute loops of a "Magic Tape (registered trademark)" or another component thereof having a large number of minute hooks).

Though not illustrated in FIGS. 1A and 1B, the ilium belt 1 may contain an elastic material in a portion(s) except the both ends thereof and the portions where the fastener components 4,4 are attached. Especially, a central portion of the belt 1 which is placed on the back side of the user's body when the belt is worn on the user's body is preferably made of the elastic material. Preferable examples of the elastic material include the materials (a) to (c) describes in the above section of "Use of Elastic Material in Ilium Belt". When the elastic material is used, the portion made of the material may have a double-belt structure. A portion having the double-belt structure or a component of the double belt may be fixed by sewing to a portion made of the flexible and strong band-shaped belt having no elasticity.

[Buttock or Lumbar Belt]

Figure 2:
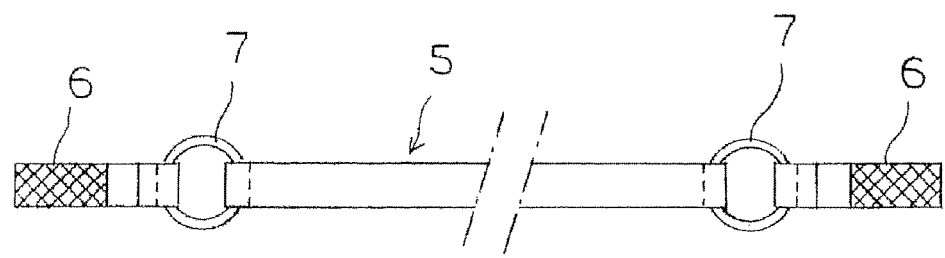
FIG. 2 is a view showing an inner surface of a buttock or lumbar belt.

A buttock belt is a belt that is wound around the user's waist, passing under the user's buttocks, lifting up the buttocks. A lumbar belt is a belt that is wound around the user's waist, passing the user's lumbar back, which is a back side of a lumbar curve located immediately above the pelvis. FIG. 2 is a rear view showing an inner surface of the buttock/lumbar belt 5 (i.e., a view of an inner surface of the belt when worn on the user's body).

The buttock/lumbar belt 5 is also a flexible and strong band-shaped belt having no elasticity made of a natural or synthetic fiber. The buttock/lumbar belt 5 has an approximately same width as the ilium belt 1, but is shorter than the ilium belt 1. Sheet-shaped fastener components 6,6 that can be reversibly bonded to the fastener components 4,4 on the ilium belt 1 are attached on the inner surface of the buttock/lumbar belt 5 on both ends thereof.

Further, rings 7,7 are attached to the buttock/lumbar belt 5 a little more inside the ends thereof than the fastener components 6,6 attached on the ends, through which the ilium belt 1 is to be placed. The buttock/lumbar belt 5 is put through each ring 7 and then is folded back. The folded-back portion is fixed to the ring 7 by sewing.

Figure 3A:
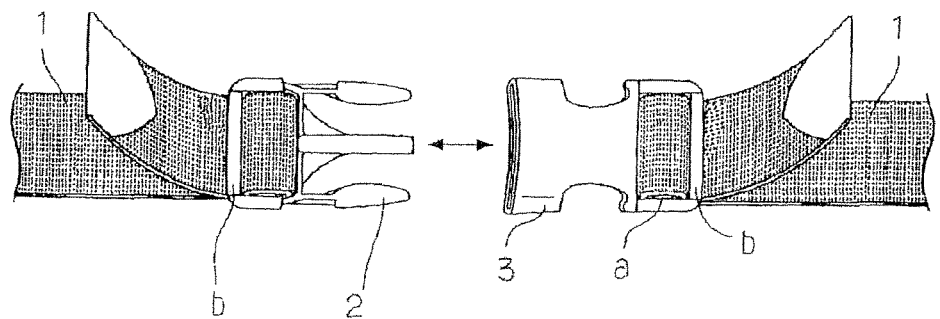
FIG. 3A is an enlarged view showing a pair of connectors attached on both ends of the ilium belt.
Figure 3B:
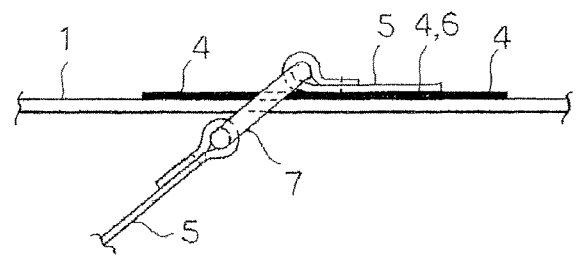
FIG. 3B shows a connection between the ilium belt and the buttock or lumbar belt via a ring.

The structure of connection between the ilium belt 1 and the buttock/lumbar belt 5 via the ring 7 is explained based on the side view shown in FIG. 3B. In FIG. 3B, outer surfaces of the ilium belt 1 and the buttock/lumbar belt 5 are placed on the upper side of the figure while the inner surfaces of the belts are placed on the lower side of the figure. While a main portion of the buttock/lumbar belt 5 is placed inside the inner surface of the ilium belt 1, an end portion of the buttock/lumbar belt 5 is placed outside the outer surface of the ilium belt 1, with the ilium belt 1 placed through the ring 7. In this configuration, the fastener component 6 on the inner surface of the buttock/lumbar belt 5 on the end thereof is bonded to the fastener component 4 on the outer surface of the ilium belt 1 in the connection area thereon.

Thus, the buttock/lumbar belt 5 can be easily put on and taken off from the ilium belt 1 since the end of the buttock/lumbar belt 5 is connected to the ilium belt 1 on the outer surface of the ilium belt 1 while the main portion of the buttock/lumbar belt 5 is placed inside the inner surface of the ilium belt 1. Further, the ring 7 allows the connection angle of the buttock/lumbar belt 5 to the ilium belt 1 to be easily changed.

Though not illustrated in FIG. 2, the buttock/lumbar belt 5 may contain an elastic material in a portion(s) except portions where the fastener component 6 and the ring 7 are attached. Especially, a central portion of the belt 5 is preferably made of the elastic material. When the elastic material is used, the portion made of the material may have a double-belt structure. In these cases, configurations similar to those in the ilium belt 1 may be adopted.

[Auxiliary Belt]

Figure 8:
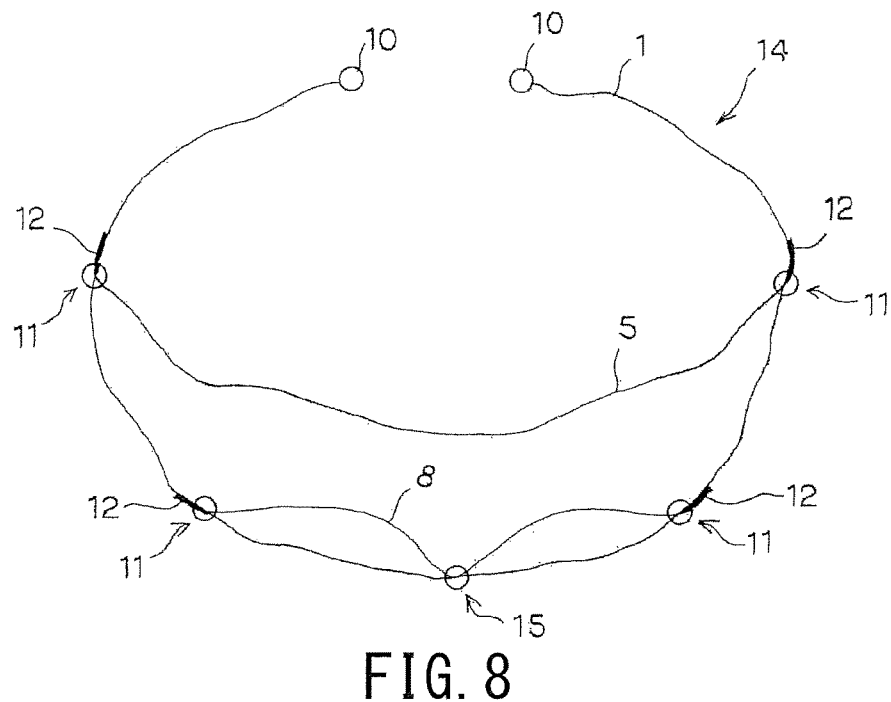
FIG. 8 is a schematic view entirely showing a sacroiliac belt according to Example 2.
Figure 9:
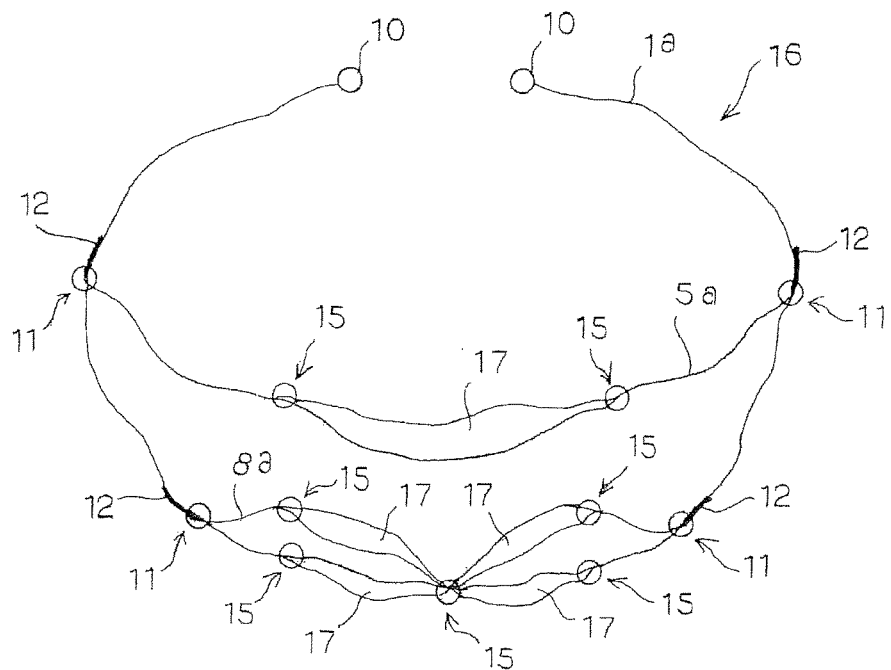
FIG. 9 is a schematic view entirely showing a sacroiliac belt according to Example 3.

An auxiliary belt is attached to the ilium belt to enhance the tightening pressure of the ilium belt to the user's pelvis. The auxiliary belt 8 is not specifically shown in the figures, but is shown in FIGS. 8 and 9 in a simplified way.

The auxiliary belt 8 is also a flexible and strong band-shaped belt having no elasticity made of a natural or synthetic fiber. The auxiliary belt 8 has an approximately same width as the ilium belt 1, but is shorter than the ilium belt 1. Sheet-shaped fastener components are attached on the inner surface of the auxiliary belt 8 on both ends thereof. The fastener components can be reversibly bonded to a pair of auxiliary connection areas placed on the outer surface of the ilium belt 1.

Rings are placed a little more inside the both ends of the auxiliary belt 8 than the fastener components attached on the ends. The ilium belt 1 is put through the rings, and is connected to the auxiliary belt 8 by the same connection structure as in the connection to the buttock/lumbar belt 5 shown in FIG. 3B. Thus, the auxiliary belt 8 can be easily put on and taken off from the ilium belt 1, as in the case of the buttock/lumbar belt 5, since the both ends of the auxiliary belt 8 is connected to the ilium belt 1 on the outer surface of the ilium belt 1 via the fastener components while the auxiliary belt is put inside the inner surface of the ilium belt 1. Further, the auxiliary belt 8 may contain an elastic material in a portion(s) except portions where the sheet-shaped fastener components and the rings are attached. Especially, a central portion of the belt 8 is preferably made of the elastic material. When the elastic material is used, the portion made of the material may have a double-belt structure. In these cases, configurations similar to those in the ilium belt 1 may be adopted.

Sacroiliac Belt According to Example 1

Figure 4:
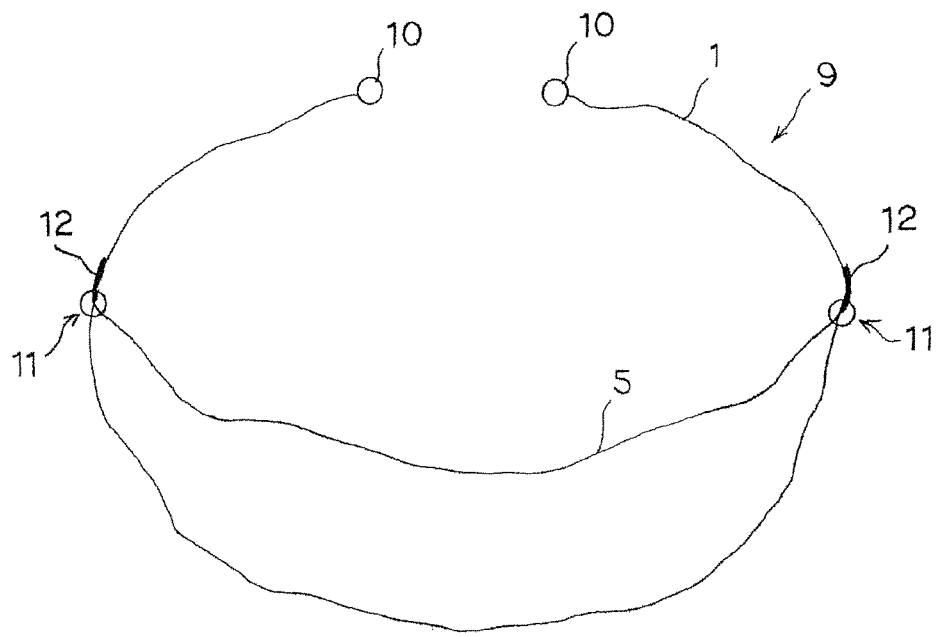
FIG. 4 is a schematic view entirely showing a sacroiliac belt according to Example 1.

An entire schematic view of a sacroiliac belt 9 according to Example 1 is shown in FIG. 4. To simply show a structure in the figure, belts are shown by single solid lines and specific structural components are shown by marks "○".

As shown in FIG. 4, the sacroiliac belt 9 has the above-described ilium belt 1 and buttock/lumbar belt 5. A pair of reversible connectors 10 (consisting of a hook and a bracket) shown in FIG. 3A is attached on the both ends of the ilium belt 1. Any portion of the ilium belt 1 (e.g., a central portion thereof) may be made of an elastic material. The buttock/lumbar belt 5 is shorter than the ilium belt 1. Any portion of the buttock/lumbar belt 5 (e.g., a central portion thereof) may be made of an elastic material.

The both ends of the buttock/lumbar belt 5 are reversibly connected to the ilium belt 1 in the connection areas by connection structures 11 via the rings and by touch fastener structures 12, as shown in FIG. 3B.

Figure 5A:
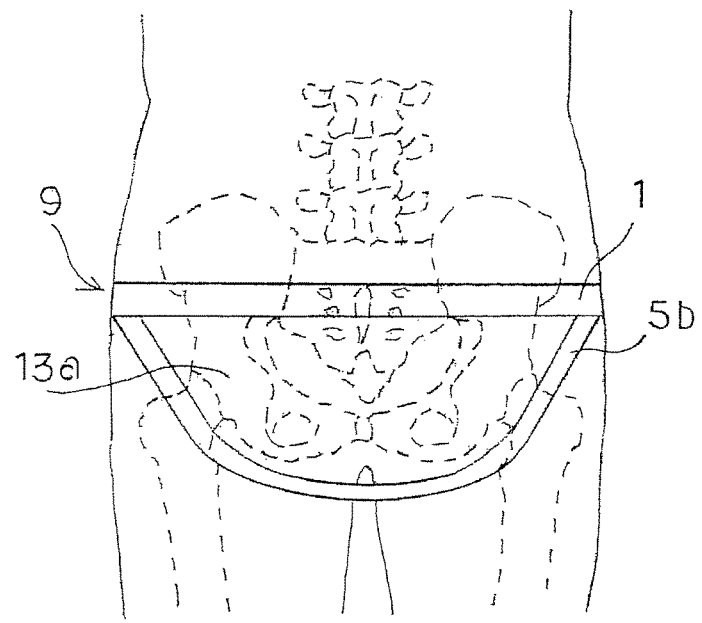
FIG. 5A is a rear view showing the sacroiliac belt where the ilium belt and the buttock belt are worn on a user's body.
Figure 5B:
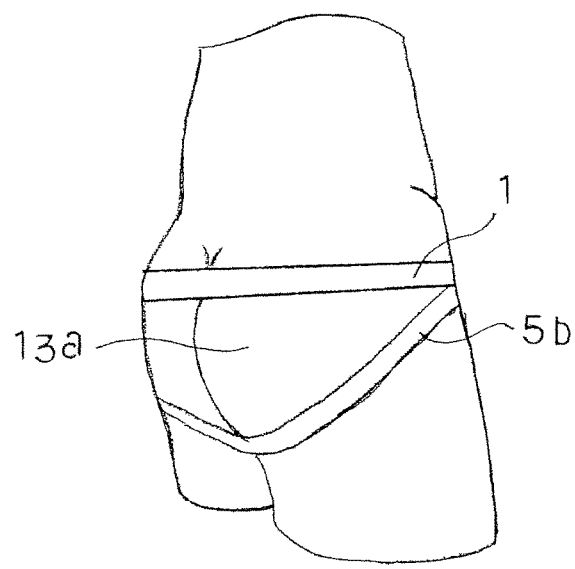
FIG. 5B is a rear perspective view of the sacroiliac belt.

When the sacroiliac belt 9 according to Example 1 has the ilium belt 1 and a buttock belt 5b, the sacroiliac belt 9 is worn on the user's body as shown in FIGS. 5A and 5B. Specifically, the ilium belt 1 is wound around the user's waist, surrounding the right and left ilia of the user, and the hook and the bracket attached on the both ends of the ilium belt 1 are fixed to each other on the front side of the user's body. The buttock belt 5b is wound around the waist passing under the user's buttocks, lifting up the buttocks. In this state, the ilium belt 1 and the buttock belt 5b form a buttock-side pelvic holding loop 13a to hold the user's pelvis from the buttock side. The loop 13a provides an excellent holding ability for the pelvis by holding the entire pelvis from the buttock side, like wrapping the pelvis.

Figure 6A:
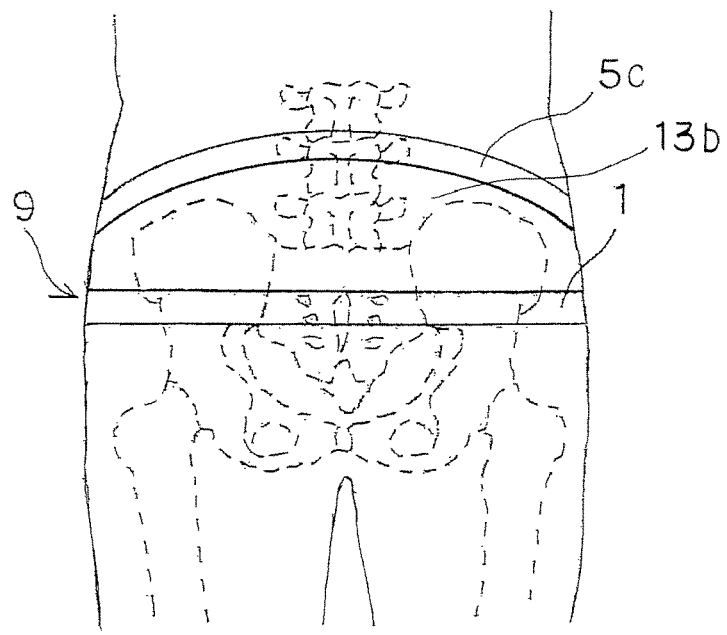
FIG. 6A is a rear view showing the sacroiliac belt where the ilium belt and the lumbar belt are worn on a user's body.
Figure 6B:
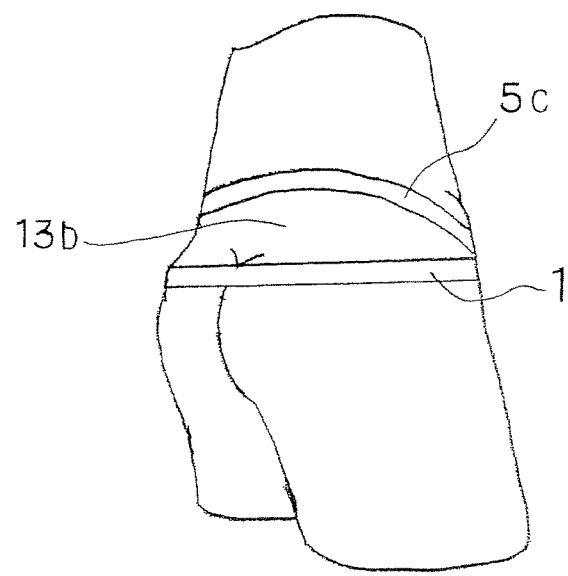
FIG. 6B is a rear perspective view of the sacroiliac belt.

On the other hand, when the sacroiliac belt 9 according to Example 1 has the ilium belt 1 and a lumbar belt 5c, the sacroiliac belt 9 is worn on the user's body as shown in FIGS. 6A and 6B. Specifically, the ilium belt 1 is wound around the user's waist, surrounding the right and left ilia of the user, and the hook and the bracket attached on the both ends of the ilium belt 1 are fixed to each other on the front side of the user's body. The lumbar belt 5c is wound around the waist passing the user's lumbar back, which is a back side of the lumbar curve immediately above the pelvis. In this state, the ilium belt 1 and the lumbar belt 5c form a lumbar-side pelvic holding loop 13b to hold the user's pelvis from the lumbar back side. The loop 13b provides an excellent holding ability for the pelvis by holding the entire pelvis from the lumbar back side, like wrapping the pelvis.

Sacroiliac Belt According to Example 2

An entire schematic view of a sacroiliac belt 14 according to Example 2 is shown in FIG. 8. To simply show a structure in the figure, belts are shown by single solid lines and specific structural components are shown by marks "○".

As shown in FIG. 8, the sacroiliac belt 14 has the above-described ilium belt 1, buttock/lumbar belt 5, and auxiliary belt 8. The configurations of the ilium belt 1 and the buttock/lumbar belt 5 and the connection structure therebetween are the same as in the sacroiliac belt 9 according to Example 1. The auxiliary belt 8 is still shorter than the buttock/lumbar belt 5. The both ends of the auxiliary belt 8 are connected to the ilium belt 1 near the central portion of the ilium belt 1, by the connection structures 11 via the rings and by the touch fastener structures 12, in the same way as shown in FIG. 3B.

Any portion of the auxiliary belt 8 (e.g., a central portion thereof) may be made of an elastic material. The central portion of the auxiliary belt 8 is connected to the central portion of the ilium belt 1 through a fixed connection 15 by sewing. Thus, when the central portions of both the ilium belt 1 and the auxiliary belt 8 are made of elastic materials, the portions of the two belts 1,8 made of the elastic materials are sewed to each other to form the fixed connection 15.

Sacroiliac Belt According to Example 3

An entire schematic view of a sacroiliac belt 16 according to Example 3 is shown in FIG. 9. To simply show a structure in the figure, belts are shown by single solid lines and specific structural components are shown by marks "○".

As shown in FIG. 9, the sacroiliac belt 16 has ilium belt 1a, buttock/lumbar belt 5a, and auxiliary belt 8a. The belts 1a, 5a, 8a have double-belt structures 17 made of elastic materials in the central portions thereof. The both ends of the double-belt structures 17 each are fixed to strong and flexible band-shaped portions of the belts 1a, 5a, 8a having no elasticity via fixed connections 15 by sewing.

The sacroiliac belt 16 according to Example 3 has the same configurations as the sacroiliac belt 14 according to Example 2 except the above-described configurations.

Sacroiliac Belts According to Other Examples

The sacroiliac belt may be worn on the user's body forming rings of the ilium belt and the buttock/lumbar belt each, as in the first and second preferred embodiment described above.

INDUSTRIAL APPLICABILITY

The present invention provides a sacroiliac belt having an excellent holding ability for a user's pelvis as well as a high tightening effect to the user's sacroiliac joints.

The invention claimed is:

1. A sacroiliac belt comprising a belt pair that forms a pelvic holding loop to hold a user's pelvis from a buttock side or a lumbar back side, entirely wrapping the pelvis, the belt pair comprising:
   a ring-shaped ilium belt (A) configured to be wound around the user's waist, surrounding the user's right and left ilia; and
   a second belt selected from:
      either a buttock belt (B1) configured to be wound around the user's waist passing under the user's buttocks, lifting up the buttocks; or
      a lumbar belt (B2) configured to be wound around the user's waist passing the user's lumbar back, which is a back side of the user's lumbar curve located immediately above the pelvis, wherein:
   the second belt is shorter than the ilium belt,
   the sacroiliac belt comprises rings at both ends of the second belt,
   while the ilium belt placed through the rings, the both ends of the second belt each connected to the ilium belt in a pair of connection areas placed inside both ends of the ilium belt through a reversible connection through which the both ends of the second belt are reversibly connected to the pair of connection areas on the ilium belt via touch fasteners that consist of first and second components, the first components attached in the connection areas on the ilium belt, the second components attached on the both ends of the second belt the first components have widths within which positions of connection between the first and second components are adjustable, the second belt comprises:
- a band-shaped main portion;
- the rings, and
- a pair of connection portions each comprising the second components of the touch fasteners, and connected to both ends of the main portion via the rings, the both ends of the main portion and the connection portions each attached to the rings in a movable manner along rims of the rings, and
- the rings are placed more inside the both ends of the second belt than the second components are.

2. The sacroiliac belt according to claim 1, wherein the pair of connection areas is placed in boundary regions between front and back sides of the ilium belt for connecting the ilium belt and the buttock belt, and the pair of connection areas is placed in a central region of the front side of the ilium belt for connecting the ilium belt and the lumbar belt.

3. The sacroiliac belt according to claim 2, wherein:
- at least a part of the ilium belt or the second belt is made of an elastic material, or
- at least a part of the ilium belt or the second belt is made of an elastic material, and the part has a double-belt structure.

4. The sacroiliac belt according to claim 3, wherein the sacroiliac belt comprises an auxiliary belt that is attached to the ilium belt and increases a tightening pressure of the ilium belt.

5. The sacroiliac belt according to claim 1, wherein the pair of connection areas is placed in boundary regions between front and back sides of the ilium belt for connecting the ilium belt and the buttock belt, and the pair of connection areas is placed in a central region of the front side of the ilium belt for connecting the ilium belt and the lumbar belt.

6. The sacroiliac belt according to claim 1, wherein:
- at least a part of the ilium belt or the second belt is made of an elastic material, or
- at least a part of the ilium belt or the second belt is made of an elastic material, and the part has a double-belt structure.

7. The sacroiliac belt according to claim 1, wherein the sacroiliac belt comprises an auxiliary belt that is attached to the ilium belt and increases a tightening pressure of the ilium belt.

8. The sacroiliac belt according to claim 1, wherein the first components have widths within which positions of connection between the first and second components are adjustable.

* * * * *